United States Patent [19]

Jongsma

[11] 4,339,599

[45] Jul. 13, 1982

[54] PROCESS FOR THE PREPARATION OF BENZENE-MONOCARBOXYLIC ACIDS

[75] Inventor: Cornelis Jongsma, Oirsbeek, Netherlands

[73] Assignee: Stamicarbon, B.V., Geleen, Netherlands

[21] Appl. No.: 242,115

[22] Filed: Mar. 9, 1981

[30] Foreign Application Priority Data

Mar. 15, 1980 [NL] Netherlands .......................... 8001550

[51] Int. Cl.$^3$ .............................................. C07C 51/16
[52] U.S. Cl. .................................................... 562/412
[58] Field of Search ......................................... 562/412

[56] References Cited

FOREIGN PATENT DOCUMENTS 7311187 8/1973 Netherlands ........................ 562/412

*Primary Examiner*—Alan Siegel
*Attorney, Agent, or Firm*—Cushman, Darby & Cushman

[57] ABSTRACT

A process for the preparing of a benzene-monocarboxylic acid by oxidation of a monoalkyl-benzene compound in the liquid phase with the aid of a gas containing molecular oxygen in the presence of a catalyst composed of a cobalt and a manganese compound, both of which are soluble in the reaction mixture, with a manganese-cobalt atomic ratio between 1:500 and 1:100,000, thus improving the selectivity of the reaction to form the desired benzene-monocarboxylic acid.

7 Claims, 1 Drawing Figure

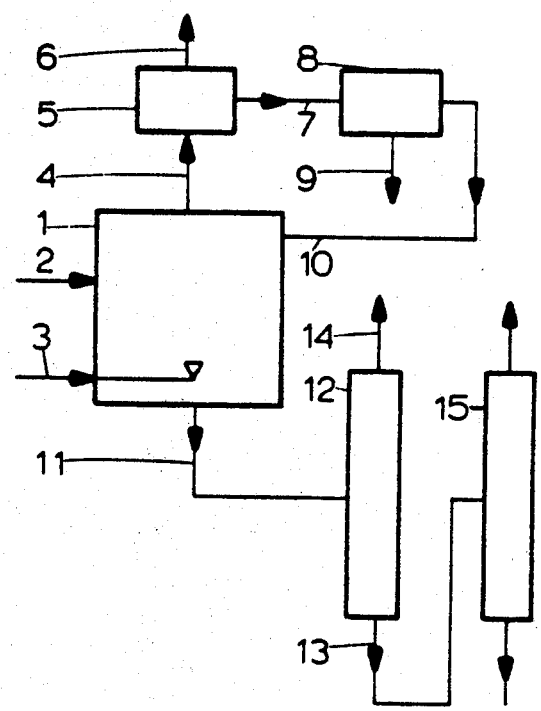

PROCESS FOR THE PREPARATION OF BENZENE-MONOCARBOXYLIC ACIDS

BACKGROUND OF THE INVENTION

The invention relates to a process for the preparation of a benzene-monocarboxylic acid by oxidation of a monoalkyl-benzene compound in the liquid phase with the aid of a gas containing molecular oxygen in the presence of a catalyst composed of a cobalt and a manganese compound, both of which are soluble in the reaction mixture. Such a process is known from Dutch patent application No. 7,311,187.

In the process according to Dutch patent application No. 7,311,187 benzoic acid is prepared by oxidizing toluene in the substantial absence of a lower fatty acid and/or a halogen compound, and in the presence of a cobalt compound and a manganese compound with a weight ratio between cobalt metal and manganese metal of less than 99,8:0,2, which means that the manganese:cobalt atomic ratio must be more than 1:466. This process has as a disadvantage that the selectivity of the reaction to form the desired benzene-monocarboxylic acid is not satisfactory.

SUMMARY OF THE INVENTION

The aim of the invention is to improve this. The process according to the invention is characterized in that a manganese:cobalt atomic ratio between 1:500 and 1:100,000 is applied. At such a low manganese:cobalt atomic ratio the selectivity of the reaction to form the desired benzene-monocarboxylic acid is significantly better than in the process according to Dutch patent application No. 7,311,187. This is a surprising result, for Dutch patent application No. 7,311,187 clearly advises not to apply manganese:cobalt atomic ratios lower than 1:466, as such a catalyst would not yield any practical improvement compared with a catalyst consisting only of a cobalt compound.

The disadvantages of the application of only a cobalt compound as catalyst are summed up in said patent application. Dutch patent application No. 7,311,187 also points out that the application of manganese:cobalt atomic ratios many times higher than 1:466 would in fact be preferable to the application of a manganese:cobalt atomic ratio of the order of magnitude of 1:466.

DESCRIPTION OF THE INVENTION

Very suitable atomic ratios between manganese and cobalt in the process according to the invention lie between 1:500 and 1:10,000, by preference between 1:600 and 1:6,000.

As manganese and cobalt preferably the salts of the benzene-monocarboxylic acid to be prepared are used. The metals can also be added in the form of, for instance, the free metals, salts of aliphatic carboxylic acids with 1-20 carbon atoms, oxides, hydroxides, complex compounds, other organic salts and alcoholates. Under the reaction conditions the salts of the benzene-monocarboxylic acid to be prepared are easily formed starting from the added materials.

The process according to the invention starts from a monoalkyl-benzene compound. Besides the alkyl group, the monoalkyl-benzene compound may contain one or more substituents that are inert under the reaction conditions, e.g. chlorine, bromine, and nitro, tertiary alkyl, alkoxy, aryloxy and cyanogen groups.

The process according to the invention is very suitable for oxidizing toluene to benzoic acid. Benzoic acid is applied, for instance, in the preparation of phenol.

The process according to the invention preferably takes place in the substantial absence of an aliphatic carboxylic acid and/or a halogen compound serving as promotor. This obviates the need to separate and purify the reaction product from the aliphatic carboxylic acid and/or the halogen compound serving as promotor, which would entail additional operations. The use of an aliphatic carboxylic acid and/or a halogen compound serving as promotor involves extra costs, for instance to make up the part of the aliphatic carboxylic acid and/or the halogen compound serving as promotor that is lost during one of the process steps and to regenerate the aliphatic carboxylic acid. To have the same quantity of monoalkyl-benzene compound react with oxygen for a certain time would require a larger reactor volume than in the process according to the preferred embodiment, because the required aliphatic carboxylic acid also takes up space. As aliphatic carboxylic acids are usually stronger acids than benzene-monocarboxylic acids, these aliphatic carboxylic acids will give rise to corrosion problems. The halogen compounds serving as promoter, too, are corrosive compounds.

The general reaction conditions in the process according to the invention are described in 'Hydrocarbon Processing', 13, (11), 173–176 (1964) and in Dutch patent application No. 7,311,187.

In the process according to the invention use can be made of substances that serve as initiator or activator of the reaction, for instance peroxides and aldehydes. Furthermore, compounds of other metals that are soluble in the reaction mixture may, besides the compounds of cobalt and manganese, be present as co-catalyst, for instance magnesium, copper, strontium zinc, cadmium, mercury, aluminum, lead, tin, antimony, bismuth, silver, nickel, iron, rubidium, cesium, hafnium, titanium, gallium, tungsten, platinum, chromium, vanadium and in particular zirconium.

The oxidation is carried out with the aid of a gas containing molecular oxygen. Examples of gases that can be used are air, oxygen-enriched air, air diluted with nitrogen, pure oxygen, ozone and mixtures of these gases.

Temperature and pressure are not critical provided a liquid phase is maintained in the reaction system during the reaction, but a temperature between 390 K. and 500 K. and a pressure between 200 kPa and 2000 kPa are to be preferred. Especially suitable are temperatures between 400 K. and 460 K. and pressures between 300 kPa and 800 kPa.

The process according to the invention can be carried out both batch-wise and continuously.

DESCRIPTION OF THE DRAWING

The invention will be elucidated with the aid of the attached reaction scheme.

To oxidation reactor 1 liquid toluene is supplied through line 2 and air through line 3. The toluene contains 10 to 1000 ppm by weight of cobaltous acetate as dissolved catalyst. In reactor 1 the toluene is oxidized in the liquid phase at a temperature of 413 to 438 K. and a pressure of 300 to 1000 kPa. Through line 4 the reactor off-gas is led to condenser 5. The non-condensable gases escape through line 6, the condensate is led through line 7 to separator 8, where it separates into an organic layer and an aqueous layer. The aqueous layer is removed through line 9. The organic layer is returned to oxidation reactor 1 through line 10. The liquid oxidation mixture flows from oxidation reactor 1 to distillation column 12 through line 11. There all components boiling at a lower temperature than benzoic acid, and by preference some benzoic acid, are distilled off and removed through line 14. This top product consists mainly of toluene and can be returned to oxidation reactor 1, either in its entirety, or after recovery of a small quantity of benzaldehyde by distillation.

The bottom product flows through line 13 to distillation column 15, in which all benzoic acid present is distilled off from the products boiling at higher temperatures, which are called tar.

EXAMPLES

The invention will be elucidated with reference to the following non-restricting examples and comparative experiments.

EXAMPLE I

In continuous oxidation reactor 1 toluene is oxidized in the liquid phase with oxygen from the air, at a temperature of 433 K. and a pressure of 500 kPa, in the presence of 80 ppm by weight of cobalt (added as acetate).

The reaction mixture further contains such a quantity of manganese (also added as acetate) that the manganese:cobalt atomic ratio is 1:3,300.

In distillation column 12 the components boiling at lower temperatures than benzoic acid and some benzoic acid are distilled off from the bottom stream of reactor 1 at atmospheric pressure. The bottom product of distillation column 12 is further distilled at atmospheric pressure in distillation column 15 until practically all benzoic acid has been removed from the reaction product. Under these conditions it is possible to recover 913 moles of benzoic acid for every 1000 moles of toluene fed to the reactor.

EXAMPLE II

Example I is repeated, this time however with a manganese:cobalt atomic ratio of 1:1000.

Again it is possible to recover 913 moles of benzoic acid for every 1000 moles of toluene fed to the reactor.

COMPARATIVE EXPERIMENT A

Example I is repeated, this time however with a manganese:cobalt atomic ratio of 1:67.

Now only 908 moles of benzoic acid can be recovered for every 1000 moles of toluene fed to the reactor.

COMPARATIVE EXPERIMENT B

Example I is repeated, this time however in the substantial absence of manganese in the reaction mixture.

Now only 909 moles of benzoic acid can be recovered for every 1000 moles of toluene fed to the reactor.

Though in the examples cobalt concentrations of about 80 ppm by weight are used, cobalt concentrations between 10 and 1000 ppm by weight are well applicable.

The manganese content is by preference at least 0,01 ppm by weight.

I claim:

1. Process for the preparation of a benzene-monocarboxylic acid by oxidation of a monoalkyl-benzene compound in the liquid phase with the aid of a gas containing molecular oxygen in the presence of a catalyst composed of a cobalt and a manganese compound, both of which are soluble in the reaction mixture, wherein the manganese:cobalt atomic ratio in said catalyst is between 1:500 and 1:100,000.

2. Process according to claim 1, wherein the atomic ratio between manganese and cobalt lies between 1:500 and 1:10,000.

3. Process according to claim 1 or 2, wherein the atomic ratio between manganese and cobalt lies between 1:600 and 1:6,000.

4. Process according to any one of the claims 1 or 2, wherein the process is carried out in the substantial absence of an aliphatic carboxylic acid and/or a halogen compound serving as promotor.

5. Process according to any one of the claims 1 or 2, wherein benzoic acid is prepared by oxidation of toluene.

6. Process according to any one of the claims 1 or 2, wherein as catalyst the relevant salts of the benzene-monocarboxylic acid are used.

7. Process according to any one of the claims 1 or 2, wherein as co-catalyst also a zirconium compound that is soluble in the reaction mixture is applied.

* * * * *